(12) United States Patent
Kano

(10) Patent No.: US 9,075,049 B2
(45) Date of Patent: Jul. 7, 2015

(54) IMMUNOASSAY METHOD AND REAGENT THEREFOR

(75) Inventor: Mayumi Kano, Gosen (JP)

(73) Assignee: DENKA SEIKEN CO., LTD., Tokyo (JP)

( * ) Notice: Subject to any disclaimer, the term of this patent is extended or adjusted under 35 U.S.C. 154(b) by 281 days.

(21) Appl. No.: 13/262,166

(22) PCT Filed: Mar. 30, 2010

(86) PCT No.: PCT/JP2010/055693
§ 371 (c)(1),
(2), (4) Date: Mar. 15, 2012

(87) PCT Pub. No.: WO2010/113943
PCT Pub. Date: Oct. 7, 2010

(65) Prior Publication Data
US 2012/0164752 A1   Jun. 28, 2012

(30) Foreign Application Priority Data

Mar. 31, 2009   (JP) ................................. 2009-085100

(51) Int. Cl.
*G01N 33/53* (2006.01)
(52) U.S. Cl.
CPC .................................. *G01N 33/5306* (2013.01)
(58) Field of Classification Search
None
See application file for complete search history.

(56) References Cited

U.S. PATENT DOCUMENTS

2010/0143933 A1   6/2010   Minakawa et al.

FOREIGN PATENT DOCUMENTS

| JP | 6-300761 A | 10/1994 |
| JP | 2003-149244 A | 5/2003 |
| JP | 2005-241415 A | 9/2005 |
| JP | 2006-126166 A | 5/2006 |

OTHER PUBLICATIONS

The International Preliminary Report on Patentability issued for PCT/JP2010/055693 on Nov. 15, 2011.*
Domingo in "Anionic Surfactants," (H.W. Stache, Ed.), Marcel Dekker, N.Y., 1996, p. 236.*
A printout retrieved from http://www.chembuyersguide.com/cas/2/27028-82-6.html on Nov. 4, 2013.*
A printout retrieved from CAS Registry on Nov. 1, 2013.*
A printout retrieved from http://en.wikipedia.org/wiki/Polysorbate_80 on Nov. 1, 2013.*
A printout retrieved from http://www.intertek.com/chemicals/hlb/ on Nov. 1, 2013.*
Cheng, H. M., "Tween 20 selectively enhances naturally occurring anticardiolipin antibody binding in ELISA procedures," Journal of Immunological Methods (1996), vol. 191, pp. 87-88.
Extended European Search Report issued Dec. 7, 2012, in European Patent Application No. 10758714.9.
Koltermann et al., "Production of a human interleukin-8 expressed in *Escherichia coli*: From a laboratory scale for in vitro tests via a technical scale for animal studies . . . ," Journal of Biotechnology (1997), vol. 54, pp. 29-42.
Lim et al., "Binary-surfactant (Brij 35 + Tween 20) assisted preparation of highly dispersed Pt nanoparticles on carbon," J. Nanopart. Res. (2008), vol. 10, pp. 1215-1220.
International Search Report, dated May 18, 2010, issued in PCT/JP2010/055693.

* cited by examiner

*Primary Examiner* — Galina Yakovleva
(74) *Attorney, Agent, or Firm* — Birch, Stewart, Kolasch & Birch, LLP

(57) ABSTRACT

[Problems] An object of the present invention is to provide a novel method which can expand the measurement range in an immunoassay method.
[Means for Solution] The immunoassay method according to the present invention comprises allowing a polyoxyethylene alkyl ether sulfate and a polyoxyethylene sorbitan fatty acid ester to coexist in a reaction system.
[Effects] According to the method of the present invention, variation (standard deviation) in blank measurement values in particular can be reduced, so that measurement values are stabilized. By this, a significant difference can be obtained in measurement values even in a low-concentration range where conventional immunoassay methods have difficulty in performing measurements; therefore, the measurement accuracy in such low-concentration range can be improved.

16 Claims, 1 Drawing Sheet

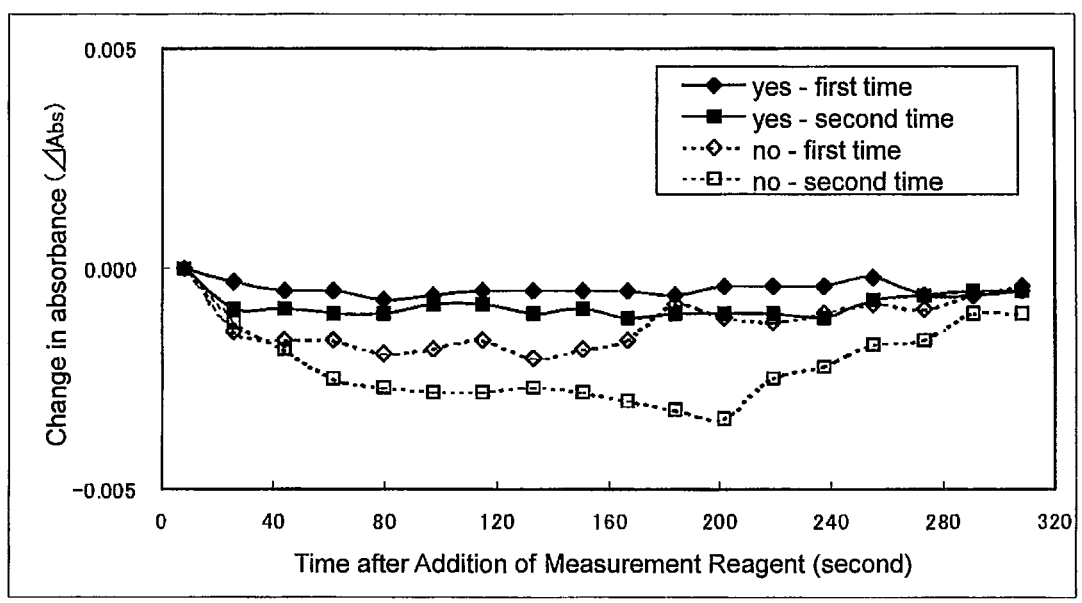

IMMUNOASSAY METHOD AND REAGENT THEREFOR

TECHNICAL FIELD

The present invention relates to a novel immunoassay method useful for measuring a low-concentration sample; and a reagent therefor.

BACKGROUND ART

Immunological analysis methods are widely used in clinical tests of serum, plasma, urine and the like since they are capable of more simply and quickly performing measurements by using an automatic analyzer.

In order to expand the use of immunological analysis methods, a reagent which has higher detection sensitivity in a low-value range and reliability than existing reagents may be demanded. Means for adding a surfactant to an immunological analysis reagent are known; however, they are often used as a means for controlling the reactivity to avoid matrix effects and the like or as a means for amplifying the change in absorbance (see Patent Documents 1 and 2).

As a method of expanding the measurable range of an immunological analysis reagent, there are a method of raising the detection upper limit of the measurement range and a method of lowering the detection lower limit.

For increasing the sensitivity by lowering the detection lower limit in the measurable range of an immunological analysis reagent, there is a method by which the sensitivity in a low-value range is increased by increasing the amount of immunobilized on particles, antibodies or antigens that are contained in the reagent. However, even when the sensitivity in a low-value range is increased, if the reproducibility is poor, good measurement accuracy in a low value-range would not be attained.

When a highly reactive component is used to increase the sensitivity in a low-value range, there are cases where the reagent stability is deteriorated and agglutination reaction proceeds during storage of the reagent due to autoagglutination, or agglutination reaction may proceed also in the blank sample due to the occurrence of non-specific agglutination.

When the sensitivity in a low-value range is increased, for example, in an automatic analyzer used for measuring the change in absorbance, since there is set an upper limit in the change in absorbance, the sensitivity in a high-value range may be limited, so that a broad measurement range may not be attained.

Since the above-described problems arise when trying to lower the detection lower limit of a measurement range, it is difficult to expand a measurable range.

PRIOR ART DOCUMENTS

Patent Documents

[Patent Document 1] JP 2005-241415 A
[Patent Document 2] JP 2006-126166 A

SUMMARY OF THE INVENTION

Problems to be Solved by the Invention

Accordingly, an object of the present invention is to provide a novel method which can expand the measurement range in an immunoassay method.

Means for Solving the Problems

The present inventor intensively studied to discover that, by allowing a polyoxyethylene alkyl ether sulfate and a polyoxyethylene sorbitan fatty acid ester to coexist in a reaction system when performing an immunoassay, variation in blank measurement values is reduced and the blank measurement values per se are also lowered, so that the accuracy of measuring a test substance in a low-concentration range can be improved, thereby completing the present invention.

That is, the present invention provides an immunoassay method which comprises allowing a polyoxyethylene alkyl ether sulfate and a polyoxyethylene sorbitan fatty acid ester to coexist in a reaction system. The present invention also provides a method of measuring a protein marker in a sample by the above-described immunoassay method according to the present invention. Further, the present invention provides a method of stabilizing measurement values in an immunoassay, which comprises allowing a polyoxyethylene alkyl ether sulfate and a polyoxyethylene sorbitan fatty acid ester to coexist in a reaction system in an immunoassay method. Still further, the present invention provides an immunoassay reagent which comprises a polyoxyethylene alkyl ether sulfate and a polyoxyethylene sorbitan fatty acid ester. Yet still further, the present invention provides an immunoassay kit which comprises the above-described immunoassay reagent according to the present invention. Moreover, the present invention provides a measurement value stabilizer for immunoassay which is composed of a polyoxyethylene alkyl ether sulfate and a polyoxyethylene sorbitan fatty acid ester.

Effects of the Invention

By the present invention, a novel means by which the accuracy of measuring a test substance in a low-concentration range can be improved in an immunoassay was provided. According to the present invention, variation (standard deviation) in blank measurement values in particular can be reduced simply by adding a prescribed substance to a reaction system, so that measurement values are stabilized. By this, a significant difference can be obtained in measurement values even in a low-concentration range where conventional immunoassay methods have difficulty in performing measurements; therefore, the measurement accuracy in such low-concentration range can be improved. The present invention is advantageous for microquantification of a substance present in a sample in a trace amount.

BRIEF DESCRIPTION OF THE DRAWINGS

FIG. 1 shows the relationships between the time (second) after addition of a measurement reagent and a change in absorbance in the agglutination immunoassays in an Example and Comparative Example of the present invention.

MODE FOR CARRYING OUT THE INVENTION

The present invention is characterized by performing an immunoassay in the presence of a polyoxyethylene alkyl ether sulfate and a polyoxyethylene sorbitan fatty acid ester. It is noted here that, unless otherwise specified, "%" herein is by mass (w/w %). Further, the term "measure" encompasses detection, quantification and semiquantification.

The polyoxyethylene alkyl ether sulfate is not particularly restricted as long as it is usually used as a surfactant. The alkyl moiety may be straight or branched, and may also contain one or more unsaturated bonds. The alkyl moiety may also be, as an alkoxy group, an inert alkyl group in which one or more carbon atoms are substituted with oxygen. Further, such alkyl group may also be partially substituted with an aryl group (for example, phenyl group), a halogen atom or the like. The number of carbon atoms in the alkyl moiety is not particularly restricted; however, it is usually 1 to 30, preferably 5 to 20, more preferably 10 to 15. A particularly preferred alkyl moiety is a saturated straight carbon chain or a straight carbon chain containing not more than several unsaturated bonds, and specific examples of such alkyl moiety include lauryl group.

The sulfate moiety may be any monovalent or higher-valent salt. Specific examples thereof include alkaline metal salts such as sodium salt and potassium salt; alkaline earth metal salts such as calcium salt and magnesium salt; ammonium salts; and amine salts, and a triethanolamine salt or sodium salt is suitably employed.

The number of oxyethylene units in the polyoxyethylene alkyl ether sulfate molecule is not particularly restricted; however, it is usually about 1 to 10.

The polyoxyethylene alkyl ether sulfate may be a single product or a mixture of two or more substances. As the polyoxyethylene alkyl ether sulfate, a commercial product marketed as a surfactant may be preferably employed.

The polyoxyethylene sorbitan fatty acid ester is not particularly restricted as long as it is usually used as a surfactant. The alkyl moiety of the fatty acid may be straight or branched, and may also contain one or more unsaturated bonds. The alkyl moiety may also be, as an alkoxy group, an inert alkyl group in which one or more carbon atoms are substituted with oxygen. Further, such alkyl group may also be partially substituted with a halogen atom or the like. The number of carbon atoms in the alkyl moiety is not particularly restricted; however, it is usually 1 to 30, preferably 5 to 25, more preferably 10 to 20. A particularly preferred alkyl moiety is a saturated straight carbon chain or a straight carbon chain containing not more than several unsaturated bonds, and specific preferred examples of the fatty acid moiety include oleic acid, stearic acid, lauric acid and palmitic acid.

The number of oxyethylene unit in the polyoxyethylene sorbitan fatty acid ester molecule is not particularly restricted; however, it is usually about 1 to 100, preferably about 5 to 60.

The polyoxyethylene sorbitan fatty acid ester may be a single product or a mixture of two or more substances. Specific examples of such composition include polyoxyethylene sorbitan monooleate and polyoxyethylene sorbitan monostearate; however, the polyoxyethylene sorbitan fatty acid ester is not restricted to these. As the polyoxyethylene sorbitan fatty acid ester, a commercial product marketed as a surfactant can be preferably employed.

As the polyoxyethylene sorbitan fatty acid ester, one having an HLB value of 10 to 20 and a number average molecular weight of 1,000 to 50,000 is suitably employed since the addition effects are prominent.

In the immunoassay method according to the present invention, the polyoxyethylene alkyl ether sulfate and the polyoxyethylene sorbitan fatty acid ester may be allowed to coexist in a reaction system in any step between the start of antigen-antibody reaction and the completion of detection and quantification of the amount of the antigen-antibody reaction; however, it is preferred that the polyoxyethylene alkyl ether sulfate and the polyoxyethylene sorbitan fatty acid ester be allowed to coexist throughout the period from the start of the antigen-antibody reaction to the detection and quantification thereof. Therefore, the polyoxyethylene alkyl ether sulfate and the polyoxyethylene sorbitan fatty acid ester can be added to the reaction system before or at the same time with the start of antigen-antibody reaction. For example, they may be added when diluting a sample or when mixing an antibody or antigen with a sample. Further, various reagents used in immunoassay may also be made to contain the polyoxyethylene alkyl ether sulfate and the polyoxyethylene sorbitan fatty acid ester in advance. For example, a buffer used for diluting a sample or a reagent containing an antibody or antigen can be made to contain these substances in advance. In the case of immunoagglutination, for example, a reagent containing insoluble carrier particles (immunobilized on particles) on which an antibody or antigen is fixed (immunobilized on) can be made to contain the polyoxyethylene alkyl ether sulfate and the polyoxyethylene sorbitan fatty acid ester in advance. Here, in cases where a B/F separation operation is performed, since the polyoxyethylene alkyl ether sulfate and the polyoxyethylene sorbitan fatty acid ester coexisting at the time of the antigen-antibody reaction are lost, it is preferred that the polyoxyethylene alkyl ether sulfate and the polyoxyethylene sorbitan fatty acid ester be added as appropriate to the reaction system by, for example, using a buffer containing them as a washing solution.

The concentration of the polyoxyethylene alkyl ether sulfate in the reaction system is preferably 0.0005 to 0.25%, more preferably 0.0125 to 0.25%. Further, the concentration of the polyoxyethylene sorbitan fatty acid ester in the reaction system is preferably 0.0005 to 0.25%, more preferably 0.0005 to 0.005%. In cases where these substances are contained in an immunoassay reagent in advance, the immunoassay reagent can be made to contain them such that their concentrations in the reaction system are in the above-described range. For example, in cases where these substances are contained in a reagent containing immunobilized on particles, the concentration of the polyoxyethylene alkyl ether sulfate in the reagent may be preferably 0.001 to 0.5%, more preferably 0.025 to 0.5%, and the concentration of the polyoxyethylene sorbitan fatty acid ester in the reagent may be preferably 0.001 to 0.5%, more preferably 0.001 to 0.01%.

Immunoassay techniques per se are well-known. The mode of the immunoassay method according to the present invention may be of any known immunoassay method; however, among known immunoassay methods, an immunoagglutination method is preferred and in particular, a latex agglutination method in which latex particles are used as insoluble carrier particles is preferred. Methods of detecting agglutination of immunobilized on particles in an immunoagglutination method are well-known, and in the present invention as well, well-known methods such as those in which the absorbance change, light scattering or the like caused by agglutination of immunobilized on particles is detected can be employed. Examples of such method include turbidimetric immunoassays (TIA method, latex agglutination method), colorimetric methods, RPLA methods, CL methods and immuno chromatography methods, and a turbidimetric method or colorimetric method which has a high sensitivity and good quantification accuracy is suitably employed.

In cases where the immunoassay is performed by an immunoagglutination method, the insoluble carrier particle used therefor is not particularly restricted and may be any well-known particle conventionally used in immunoassay reagents. Examples of such particles include latex particles of polyethylene, polystyrene or the like, alumina particles, silica particles, gold colloid particles and magnetic particles. Among these insoluble carriers, latex particles, especially polystyrene latex particles are suitably used. The size of the latex particles is not particularly restricted; however, it is preferably 30 to 600 nm.

Specific examples of the subject to be measured by immunoassay in the present invention include protein markers such as C-reactive protein (CRP), ferritin (FER), myoglobin (Mb), prostate-specific antigen (PSA), β-2 microglobulin (BMG), megalin and podocalyxin; bacteria such as *Escherichia coli*; viruses such as influenza virus, norovirus, RS virus; and antibodies thereto. A preferred subject to be measured is a marker protein which serves as a marker for a variety of diseases and the like.

The sample used in the immunoassay is not particularly restricted as long as it can contain a subject to be measured; however, body fluids such as blood, serum, plasma, urine, feces, saliva, tissue fluids, spinal fluid and swabs as well as dilutions thereof are preferred, and blood, serum, plasma, urine, feces and spinal fluid or dilutions thereof are more preferred.

The blank sample used in the immunoassay is not restricted as long as it cannot contain the subject to be measured, and purified water, physiological sline, buffer solution and negative sample or its dilution are preferred.

Immunoagglutination method per se is well-known and thus it is not necessary to explain it here. Briefly, for example, in cases where an antigen in a test sample is to be measured, an antibody which undergoes antigen-antibody reaction with the antigen to be measured, or an antigen-binding fragment thereof, is immobilized on the above-described insoluble carrier particles. The method of immobilization is also well-known, and the immobilization is carried out by a well-known method such as one utilizing physical adsorption or covalent bond. Upon mixing a suspension of the obtained immunobilized on particles and a test sample, the immunobilized on particles are agglutinated by the antigen to be measured contained in the test sample, so that the absorbance of the suspension of the immunobilized on particles is changed. The amount of the change (end-point method) or the rate of the change (rate method) is measured. A plurality of standard samples containing the antigen to be measured at various known concentrations are prepared, and the standard samples are measured for the amount of change or the rate of change in the absorbance is measured by the above-described method. A calibration curve is drawn by plotting the concentration of the antigen to be measured in the standard sample along the abscissa and plotting the amount of change or the rate of change in the absorbance along the ordinate. The antigen in a test sample containing an unknown amount of the antigen is subjected to the same method and the amount of change or the rate of change in the absorbance is measured. By applying the measurement result to the calibration curve, the antigen in the test sample can be quantified. Various automatic apparatuses conducting such an immunoagglutination method are commercially available, and the immunoagglutination method can be carried out easily and simply using the commercially available automatic apparatuses for immunoagglutination method.

As described in the examples below, by performing an immunoassay in the presence of a polyoxyethylene alkyl ether sulfate and a polyoxyethylene sorbitan fatty acid ester, fluctuations in the measurement values of blank and low-concentration samples (in the examples below, 0.005 mg/dL of CRP) are reduced and stabilized. That is, the standard deviation of the measurement values becomes small. As a result, since the significant difference between the measurement values of the blank and those of the respective low-concentration samples becomes large, for example, in the case of CRP, the analytical accuracy in a low-concentration range of about 0 to 0.005 mg/dL is improved. Therefore, the analytical method according to the present invention is extremely advantageous for measuring a test sample in a trace amount.

The above-described various reagents for immunoassay which are made to contain a polyoxyethylene alkyl ether sulfate and a polyoxyethylene sorbitan fatty acid ester in advance can be provided as immunoassay reagents used in the above-described method according to the present invention. The immunoassay reagent according to the present invention encompasses a variety of reagents that are used in an immunoassay. Examples of such reagents include sample dilutions, antibody/antigen dilutions, immobilized antibodies/antigens, immunobilized on particle suspensions, washing solutions, enzyme solutions, substrate solutions and test substance standard solutions for preparing a calibration curve.

As the immunoassay reagent according to the present invention, an immunoagglutination reagent such as a latex agglutination reagent, more specifically, a reagent containing immunobilized on particles is preferred. The concentration of the immunobilized on particles in the immunoassay reagent is not particularly restricted; however, it is preferably 0.01 to 0.5%. In the immunobilized on particle suspension, the antibody amount and the antigen amount may be any amount used in conventional methods and are not particularly restricted; however, for example, in the case of antibody-immobilized on latex, it is preferred that the amount of antibody in the latex suspension be 0.01 to 2.0 mg/mL.

In the immunoassay reagent according to the present invention, the concentration of the polyoxyethylene alkyl ether sulfate is preferably 0.0005 to 0.25%, more preferably 0.0125 to 0.25%, and the concentration of the polyoxyethylene sorbitan fatty acid ester is preferably 0.0005 to 0.25%, more preferably 0.0005 to 0.005%.

Further, the polyoxyethylene alkyl ether sulfate and the polyoxyethylene sorbitan fatty acid ester may also be provided as a measurement value stabilizer for immunoassay. The term "stabilization of measurement values" herein means, as mentioned above, to make the standard deviation of measurement values small. The stabilizer is preferably added to a variety of reagents used in immunoassay.

The above-described immunoassay reagent according to the present invention can be provided as an immunoassay kit along with, for example, a conventional reagent which does not contain a polyoxyethylene alkyl ether sulfate and a polyoxyethylene sorbitan fatty acid ester. Alternatively, the immunoassay kit according to the present invention may be one which comprises a conventional immunoassay reagent(s) and the above-described measurement value stabilizer according to the present invention in combination.

EXAMPLES

The present invention will now be described more concretely by way of examples thereof. However, the present invention is not restricted to the following examples.

Example 1

(Reagents Used)

Using antibodies to C-reactive protein (CRP), ferritin (FER) and myoglobin (Mb), measurement reagents for immunoagglutination method were prepared as follows.

Immunobilized on particles which support 0.08 mg of one of anti-CRP antibody, anti-FER antibody and anti-Mb antibody with respect to 1 mL of a suspension of polystyrene latex having an average particle size of 190 nm were suspended in a buffer (Tris, pH 8.0) to a concentration of 0.1% to prepare a latex suspension.

Surfactants were added to the thus obtained latex suspension as shown below to prepare measurement reagents of the respective proteins (CRP, FER and Mb). As Comparative Example, a latex suspension to which the above-described surfactant components were not added was used.

Measurement Reagent (Example):

| Latex suspension | | |
|---|---|---|
| + | Surfactant 1 | 0.1% |
| | Surfactant 2 | 0.005% |

Measurement Reagent (Comparative Example):
Latex suspension alone
Surfactant 1:
Triethanolamine polyoxyethylene alkyl ether sulfate ("EMAL 20T" (trade name) manufactured by Kao Corporation; mainly composed of triethanolamine polyoxyethylene lauryl ether sulfate)
Surfactant 2:
Polyoxyethylene sorbitan fatty acid ester ("Tween 80" (trade name) manufactured by Wako Pure Chemical Industries, Ltd.; mainly composed of polyoxyethylene sorbitan monooleate, HLB=15, number average molecular weight=5,000)

(Measurement by Automatic Analyzer)
Using HITACHI 7180 Automatic Analyzer as an automatic analyzer, measurements were automatically performed by an end-point method.

Using the above-described measurement reagents, physiological saline (blank) sample solution was measured for a total of 10 times. To 2.4 µL of the sample solution, 120 µL of a buffer (Tris, pH 8.5) was added, and the resultant was mixed with stirring at 37° C. After leaving the resulting mixture to stand for 5 minutes, 120 µL of the respective measurement reagents prepared in the above was added and further mixed with stirring at 37° C. The agglutination reaction was measured for about 5 minutes in terms of the change in the absorbance and the standard deviation was calculated.

(Results)
The measurement results are shown in the following Table 1.

TABLE 1

| | Name of measurement reagent | | | | | |
|---|---|---|---|---|---|---|
| | CRP measurement reagent | | FER measurement reagent | | Mb measurement reagent | |
| Addition of surfactant | no | yes | no | yes | no | yes |
| Standard deviation (SD) | 3.7 | 2.0 | 4.7 | 1.3 | 3.5 | 2.1 |
| | Comparative Example | Example | Comparative Example | Example | Comparative Example | Example |

(Discussion)
It was shown that the standard deviation of the blank became small and the accuracy of the blank was improved by adding the triethanolamine polyoxyethylene alkyl ether sulfate and polyoxyethylene sorbitan fatty acid ester. Further, it was shown that the effects of adding the above-described components can be attained regardless of the antibody type.

The reason why the accuracy of the blank was promoted is, as shown in FIG. 1, that the variation in the absorbance with the time after addition of the measurement reagent was reduced by adding triethanolamine polyoxyethylene alkyl ether sulfate and polyoxyethylene sorbitan fatty acid ester. Since this effect to reduce the variation was not changed even when the measurement was repeated twice, it was confirmed that this effect is reproducible.

Example 2

(Reagents Used)
Immobilized on particles which support 0.06 mg of anti-CRP antibody with respect to 1 mL of a suspension of polystyrene latex having an average particle size of 150 nm were suspended in a buffer (Tris, pH 8.0) to a concentration of 0.12% to prepare a latex suspension.

Surfactants were added to the thus obtained latex suspension as shown below to prepare three types of CRP measurement reagents.

Reagent No. 2-1 (Example):

| Latex suspension | | |
|---|---|---|
| + | Surfactant 1 | 0.1% |
| | Surfactant 2 | 0.005% |

Reagent No. 2-2 (Comparative Example):

| Latex suspension | | |
|---|---|---|
| + | Surfactant 1 | 0.1% |

Reagent No. 2-3 (Comparative Example):
Latex suspension alone
Surfactant 1:
Triethanolamine polyoxyethylene alkyl ether sulfate (supra)
Surfactant 2:
Polyoxyethylene sorbitan fatty acid ester (supra)

(Measurement by Automatic Analyzer)
Using HITACHI 7180 Automatic Analyzer as an automatic analyzer, measurements were automatically performed by an end-point method.

Sample solutions were each measured 10 times using the above-described three types of CRP measurement reagents. As the sample solutions, a physiological saline (blank) and a physiological saline (CRP) containing CRP in a concentration of 0.005 mg/dL were used. To 2.4 µL of each sample solution, 120 µL of a buffer (Tris, pH 8.5) was added, and the resultant was mixed with stirring at 37° C. After leaving the resulting mixture to stand for 5 minutes, 120 μL of the respective CRP measurement reagents prepared in the above was added and further mixed with stirring at 37° C. The agglutination reaction was measured for about 5 minutes in terms of the change in the absorbance.

(Results)

From the data obtained by measuring each sample 10 times, the average and standard deviation thereof were calculated and the value represented by the following equation (hereinafter, simply referred to as "difference") was determined to evaluate the measurement accuracy. The difference determined by the following equation serves as an index of the significant difference between the measurement values of the blank and those of the respective CRP sample, and a larger difference indicates a greater significant difference between the measurement values.

[CRP average value−2×(CRP SD)]−[Blank average value+2×(Blank SD)]

TABLE 2

|  | Reagent No. | | | | | |
|---|---|---|---|---|---|---|
|  | 2-1 | | 2-2 | | 2-3 | |
| Sample | Blank | CRP | Blank | CRP | Blank | CRP |
| Average ΔAbs × 10,000 | −3.6 | 7.2 | −3.8 | 8.2 | 1.6 | 17.1 |
| Standard deviation (SD) | 2.62 | 1.50 | 3.21 | 2.20 | 4.95 | 2.94 |
| Difference |  | 2.56 |  | 1.18 |  | −0.28 |
|  |  | Example |  | Comparative Example |  | Comparative Example |

(Discussion)

By adding the surfactants, the standard deviations (SD) in the measurement data of the blank and CRP samples became small and the difference between the measurement values of the sample having a CRP concentration of 0 mg/dL (blank) and those of the sample having a CRP concentration of 0.005 mg/dL (CRP sample), which was calculated using the above-described equation, became large. The standard deviation (SD) value became particularly small for the blank. Thus, the difference between the measurement values of the sample having a CRP concentration of 0 mg/dL and those of the sample having a CRP concentration of 0.005 mg/dl was increased; therefore, it was shown that the measurable range was broadened in the low-concentration side.

Example 3

(Reagents Used)

Immobilized on particles which support 0.04 mg of anti-CRP antibody with respect to 1 mL of a suspension of polystyrene latex having an average particle size of 190 nm were suspended in a buffer (Tris, pH 8.0) to a concentration of 0.1% to prepare a latex suspension.

Surfactants were added to the thus prepared latex suspension as described below to prepare five types of CRP measurement reagents each having a different concentration of Surfactant 1.

Reagent No. 3-1 (Comparative Example)

| Latex suspension | | |
|---|---|---|
| + | Surfactant 1 | 0% |
|  | Surfactant 2 | 0.005% |

Reagent No. 3-2 (Example)

| Latex suspension | | |
|---|---|---|
| + | Surfactant 1 | 0.01% |
|  | Surfactant 2 | 0.005% |

Reagent No. 3-3 (Example)

| Latex suspension | | |
|---|---|---|
| + | Surfactant 1 | 0.05% |
|  | Surfactant 2 | 0.005% |

Reagent No. 3-4 (Example)

| Latex suspension | | |
|---|---|---|
| + | Surfactant 1 | 0.10% |
|  | Surfactant 2 | 0.005% |

Reagent No. 3-5 (Example)

| Latex suspension | | |
|---|---|---|
| + | Surfactant 1 | 0.20% |
|  | Surfactant 2 | 0.005% |

Surfactant 1:

Triethanolamine polyoxyethylene alkyl ether sulfate (supra)

Surfactant 2:

Polyoxyethylene sorbitan fatty acid ester (supra)

(Measurement by Automatic Analyzer)

Using HITACHI 7180 Automatic Analyzer as an automatic analyzer, measurements were automatically performed by an end-point method.

Using the above-described five types of CRP measurement reagents, physiological saline (blank) sample solution was measured 5 times for each reagent and an average of the measurements was taken. To 2.4 μL of each sample solution, 120 μL of a buffer (Tris, pH 8.5) was added, and the resultant was mixed with stirring at 37° C. After leaving the resulting mixture to stand for 5 minutes, 120 μL of the respective CRP measurement reagents prepared in the above was added and further mixed with stirring at 37° C. The agglutination reaction was measured for about 5 minutes in terms of the change in the absorbance to compare the average changes in the absorbance.

TABLE 3

|  | Reagent No. | | | | |
|---|---|---|---|---|---|
|  | 3-1 | 3-2 | 3-3 | 3-4 | 3-5 |
| Concentration of triethanolamine polyoxyethylene alkyl ether sulfate (%) | 0.00 | 0.01 | 0.05 | 0.10 | 0.20 |

TABLE 3-continued

| | Reagent No. | | | | |
|---|---|---|---|---|---|
| | 3-1 | 3-2 | 3-3 | 3-4 | 3-5 |
| Change in absorbance (ΔAbs × 10,000) | 61.3 | 6.6 | −3.2 | −5.5 | −3.9 |
| | Comparative Example | Example | Example | Example | Example |

(Discussion)

It was confirmed that the change in the absorbance during the measurement of the physiological saline (blank) became small and non-specific agglutination was markedly suppressed by the addition of triethanolamine polyoxyethylene alkyl ether sulfate. By this, it was shown that the reagent stability in a low measurement concentration range was improved.

The invention claimed is:

1. A method of reducing variation in blank measurement values in an immunoassay, comprising:
   mixing a polyoxyethylene alkyl ether sulfate and a polyoxyethylene sorbitan fatty acid ester, an antigen or an antibody, and a test sample in a reaction system for said immunoassay;
   wherein the concentration of said polyoxyethylene alkyl ether sulfate is 0.0125% to 0.25%, and the concentration of said polyoxyethylene sorbitan fatty acid ester is 0.001% to 0.01%, in said reaction system, thereby reducing variation in the blank measurement values in said immunoassay.

2. The method according to claim 1, wherein said polyoxyethylene sorbitan fatty acid ester has an HLB value of 10 to 20.

3. The method according to claim 1, wherein said polyoxyethylene sorbitan fatty acid ester has a number average molecular weight of 1,000 to 50,000 Daltons.

4. The method according to claim 1, wherein said polyoxyethylene alkyl ether sulfate is triethanolamine polyoxyethylene lauryl ether sulfate.

5. The method according to claim 1, wherein said polyoxyethylene sorbitan fatty acid ester is polyoxyethylene sorbitan monooleate.

6. The method according to claim 1, wherein the immunoassay is an immunoagglutination method.

7. The method according to claim 6, wherein the immunoassay is a latex agglutination method.

8. The method of claim 1, further comprising measuring a marker protein in the test sample.

9. The method of claim 1, wherein the immunoassay is a latex agglutination immunoassay, wherein the polyoxyethylene alkyl ether sulfate is triethanolamine polyoxyethylene lauryl ether sulfate, wherein the polyoxyethylene sorbitan fatty acid ester is polyoxyethylene sorbitan monooleate and wherein the method comprises immobilizing an anti-C-reactive protein antibody on latex particles and measuring an amount of C reactive protein in a sample.

10. The method of claim 1, further comprising:
    detecting and/or quantifying an amount of an antigen-antibody reaction in the test sample, said detecting or quantifying is done by comparing the amount of the antibody-antigen reaction in the test sample to measurements of a blank control sample, said blank control sample comprising polyoxyethylene alkyl ether sulfate and polyoxyethylene sorbitan fatty acid ester but not the antigen or antibody,
    wherein a standard deviation of the measurements of the blank control sample is less than a standard deviation of a blank sample which does not comprise the polyoxyethylene alkyl ether sulfate and the polyoxyethylene sorbitan fatty acid ester.

11. The method of claim 10, wherein the immunoassay is a latex agglutination immunoassay, wherein the polyoxyethylene alkyl ether sulfate is triethanolamine polyoxyethylene lauryl ether sulfate, and wherein the polyoxyethylene sorbitan fatty acid ester is polyoxyethylene sorbitan monooleate.

12. The method according to claim 1, wherein the polyoxyethylene alkyl ether sulfate and a polyoxyethylene sorbitan fatty acid ester are added prior to a reaction between said antigen and antibody.

13. The method according to claim 1, wherein the polyoxyethylene alkyl ether sulfate and a polyoxyethylene sorbitan fatty acid ester are added at the same time of a reaction between said antigen and antibody.

14. The method according to claim 1, wherein the polyoxyethylene alkyl ether sulfate and a polyoxyethylene sorbitan fatty acid ester are added when diluting the sample.

15. The method according to claim 1, wherein the polyoxyethylene alkyl ether sulfate and a polyoxyethylene sorbitan fatty acid ester are added when mixing the antibody or antigen with the sample.

16. A method of stabilizing measurement values in an immunoassay, which comprises adding a polyoxyethylene alkyl ether sulfate and a polyoxyethylene sorbitan fatty acid ester in a reaction system for said immunoassay;
    wherein the concentration of said polyoxyethylene alkyl ether sulfate is 0.0125% to 0.25%, and the concentration of said polyoxyethylene sorbitan fatty acid ester is 0.001% to 0.01%, in said reaction system, thereby stabilizing the measurement values in said immunoassay.

* * * * *